United States Patent
Sato (10) Patent No.: US 11,582,928 B2
(45) Date of Patent: Feb. 21, 2023

(54) NEW GUINEA IMPATIENS VARIETY SAKIMP062

(71) Applicant: Sakata Seed Corporation, Yokohama (JP)

(72) Inventor: Chihiro Sato, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 17/315,633

(22) Filed: May 10, 2021

(65) Prior Publication Data
US 2022/0354078 A1 Nov. 10, 2022

(51) Int. Cl.
*A01H 5/02* (2018.01)
*A01H 6/16* (2018.01)

(52) U.S. Cl.
CPC ............... *A01H 6/165* (2018.05); *A01H 5/02* (2013.01)

(58) Field of Classification Search
CPC .............. A01H 6/165; A01H 6/16; A01H 5/02
USPC ...................................... Plt./318.6
See application file for complete search history.

(56) References Cited

U.S. PATENT DOCUMENTS 10,687,491 B2 * 6/2020 Sato .................. A01H 6/165
11,412,676 B1 * 8/2022 Sato .................. A01H 6/165

* cited by examiner

*Primary Examiner* — Kent L Bell
(74) *Attorney, Agent, or Firm* — Weatherly IP Solutions, LLC; James Weatherly; H. Victoria Bryant (57) ABSTRACT

A New Guinea Impatiens plant designated SAKIMP062 is disclosed. Embodiments include seeds of New Guinea Impatiens SAKIMP062, plants of New Guinea Impatiens SAKIMP062, to plant parts of New Guinea Impatiens SAKIMP062, and methods for producing an impatiens plant produced by crossing New Guinea Impatiens SAKIMP062 with itself or with another impatiens variety. Embodiments include methods for producing an impatiens plant containing in its genetic material one or more genes or transgenes and transgenic impatiens plants and plant parts produced by those methods. Embodiments also relate to impatiens varieties, breeding varieties, plant parts, and cells derived from New Guinea Impatiens SAKIMP062, methods for producing other impatiens lines or plant parts derived from New Guinea Impatiens SAKIMP062, and the impatiens plants, varieties, and their parts derived from use of those methods. Embodiments further include hybrid impatiens seeds, plants, and plant parts produced by crossing New Guinea Impatiens SAKIMP062 with another impatiens variety.

20 Claims, 2 Drawing Sheets
(2 of 2 Drawing Sheet(s) Filed in Color)

NEW GUINEA IMPATIENS VARIETY SAKIMP062

BACKGROUND

All publications cited in this application are herein incorporated by reference. New Guinea Impatiens is a species of flowering plants in the family Balsaminaeceae.

New Guinea Impatiens can be propagated from seed, cuttings, and tissue culture. Seed, cuttings and tissue culture germination protocols for New Guinea Impatiens are well-known in the art.

New Guinea Impatiens is an important and valuable ornamental plant. Thus, a continuing goal of ornamental plant breeders is to develop plants with novel characteristics, such as color, growth habit, and hardiness. To accomplish this goal, the breeder must select and develop plants that have traits that result in superior New Guinea Impatiens varieties.

The foregoing examples of the related art and limitations related therewith are intended to be illustrative and not exclusive. Other limitations of the related art will become apparent to those of skill in the art upon a reading of the specification.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

SUMMARY

Figure 1:
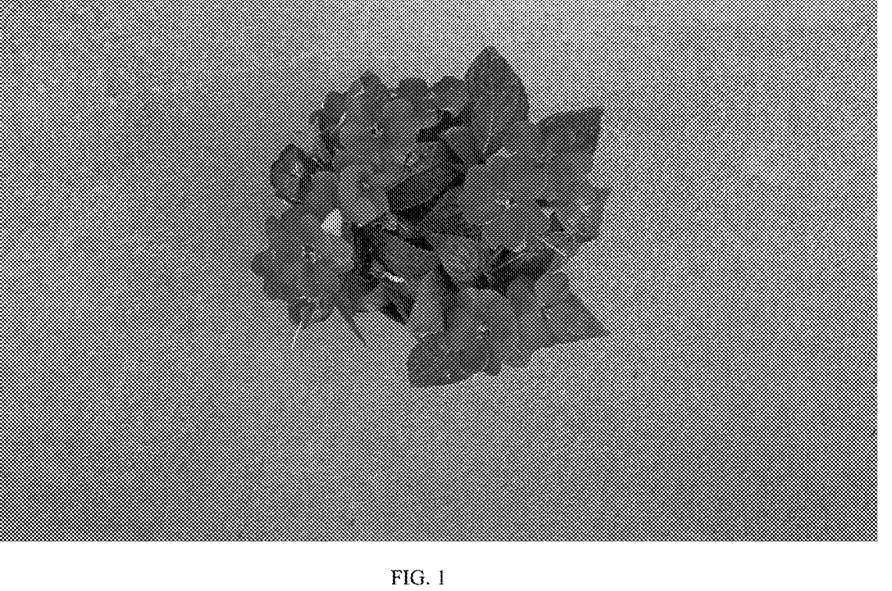
FIG. 1 shows the overall plant habit of the plant grown in a pot, including flowers and foliage.
Figure 2:
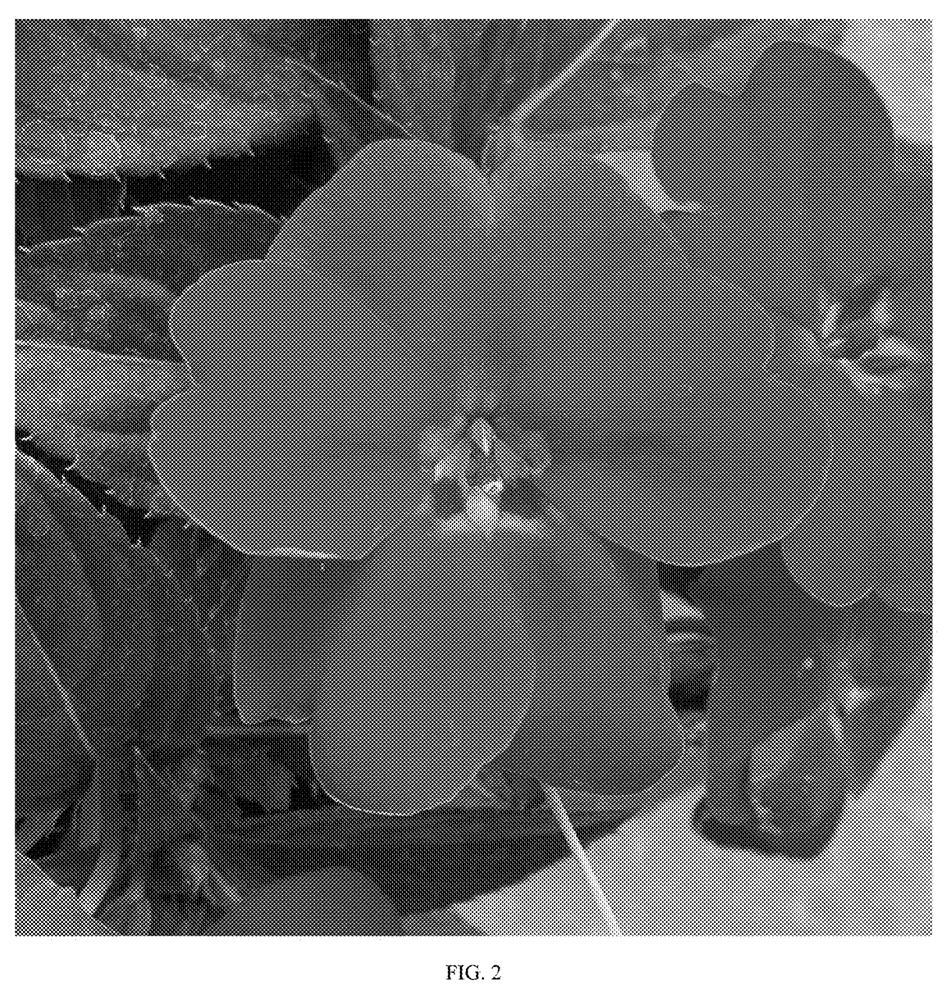
FIG. 2 shows a close-up of a mature flower of the plant.

The following embodiments and aspects thereof are described in conjunction with systems, tools and methods which are meant to be exemplary, not limiting in scope.

According to one embodiment, there is provided a New Guinea Impatiens plant which is valued as breeding line enabling the development of superior ornamental New Guinea Impatiens plants.

Another embodiment discloses a New Guinea Impatiens plant, wherein a sample of representative sample of plant tissue of said New Guinea Impatiens is deposited with a Budapest Depository.

Another embodiment relates to tissue culture produced from protoplasts or cells from the New Guinea Impatiens plants disclosed in the subject application, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, and stems.

Another embodiment relates to a plant, or a part thereof, produced by growing New Guinea Impatiens SAKIMP062, wherein the plant part comprises at least one cell of New Guinea Impatiens SAKIMP062.

Another embodiment relates to a tissue or cell culture of regenerable cells produced from the plant of SAKIMP062 and a New Guinea Impatiens plant regenerated from the tissue or cell culture of SAKIMP062.

Another embodiment relates to a method of vegetatively propagating the plant of SAKIMP062, comprising the steps of: collecting tissue or cells capable of being propagated from a plant of SAKIMP062; cultivating said tissue or cells to obtain proliferated shoots; and rooting said proliferated shoots to obtain rooted plantlets; or cultivating said tissue or cells to obtain proliferated shoots, or to obtain plantlets and a plant produced by growing the plantlets or proliferated shoots of said plant.

A further embodiment relates to a method for producing a New Guinea Impatiens seed or embryo, wherein the method comprises crossing a SAKIMP062 plant with a different New Guinea Impatiens plant and harvesting the resultant New Guinea Impatiens seed or embryo.

A further embodiment relates to a method for developing a New Guinea Impatiens plant in a New Guinea Impatiens plant breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the New Guinea Impatiens plant of SAKIMP062, or its parts, wherein application of said techniques results in development of a New Guinea Impatiens plant.

A further embodiment relates to a method of introducing a mutation into the genome of a New Guinea Impatiens plant SAKIMP062, said method comprising mutagenesis of the plant, or plant part thereof, of SAKIMP062, wherein said mutagenesis is selected from the group consisting of temperature, long-term seed storage, tissue culture conditions, ionizing radiation, chemical mutagens, and targeting induced local lesions in genomes, and wherein the resulting plant comprises at least one genome mutation and producing plants therefrom.

A further embodiment relates to a method of editing the genome of New Guinea Impatiens plant SAKIMP062, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system, and plants produced therefrom.

A further embodiment relates to a New Guinea Impatiens seed produced by growing SAKIMP062.

A further embodiment relates to a method of producing a New Guinea Impatiens plant, or part thereof, by growing a seed produced on SAKIMP062.

In addition to the exemplary aspects and embodiments described above, further aspects and embodiments will become apparent by study of the following descriptions.

DETAILED DESCRIPTION

New Guinea Impatiens variety SAKIMP062 disclosed in the present application has shown uniformity and stability, as described in the following section via vegetative cuttings and tissue culture. New Guinea Impatiens variety SAKIMP062 disclosed in the present application has been asexually reproduced a sufficient number of generations with careful attention to uniformity of plant type and has been increased with continued observation for uniformity. Additionally, New Guinea Impatiens variety SAKIMP062 produces viable pollen and is capable of being used as a parental line in breeding programs.

Origin of SAKIMP062

SAKIMP062 is botanically known as Impatiens x hybrid hort. 'SAKIMP062' originated from an interspecific hybridization between Impatiens 'NM-2124-7H', an unpatented proprietary magenta flowered Impatiens breeding line and Impatiens 'NN-1616wB', an unpatented proprietary rose flowered Impatiens breeding line in Misato, Japan.

In September 2016, the female parent line 'NM-2124-7H' and male parent line 'NN-1616wB' were crossed and a population of $F_1$ plants was created. The $F_1$ plants were evaluated in Misato, Japan in an open field trial. The criteria for plant selection included bright purple flower color, compact plant habit, and strong root system. At the completion of the trial, one single-plant selection was made based on the above criteria and vegetatively propagated. From June to August 2018, the selection was evaluated in an open field in Misato, Japan. Shoot-tip cuttings of the variety were then shipped to Salinas, Calif., where the plants were regenerated and reevaluated for stability of traits. The selection subsequently was named 'SAKIMP062' and found to have its unique characteristics reproduce true to type in successive generations of asexual propagation.

Environmental Conditions for Plant Growth

The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Data in Table 1 were taken in Salinas, Calif. Data obtained from plants grown 5.25 months from transplant into quart sized pots from rooted cuttings in Salinas, Calif., under greenhouse conditions.

The following traits and characteristics describe the new variety. Color references are to the Royal Horticultural Society Colour Chart, 6th edition. Anatomic labels are from The Cambridge Illustrated Glossary of Botanical Terms, by M. Hickey and C. King, Cambridge University Press.

TABLE 1

VARIETY DESCRIPTION INFORMATION

| Characteristic | SAKIMP062 |
|---|---|
| Family: | *Balsaminaceae* |
| Species: | *Impatiens* intergeneric hybrid (*Impatiens* x hybrida hort) |
| Common Name: | *Impatiens* |
| Parentage | |
| Female Parent: | NM-2124-7H |
| Male Parent: | NN-1616wB |
| General Appearance, Growth, and Propagation | |
| Plant Habit: | Compact |
| Plant Height: | Approximately 9.0 cm |
| Plant Spread: | Approximately 25.0 cm |
| Number of Main Branches: | 1 |
| Length of Main Branches | Approximately 8.0 mm soil line to first node; 6 cm from start to inflorescences |
| Diameter of Main Branches | Approximately 1.0 cm |
| Color of Main Branches | RHS 187B (Dark Red) |
| Number of Secondary Branches | 3 |
| Length of Secondary Branches | Approximately 5.0 cm from start to start of inflorescences |
| Diameter of Secondary Branches | Approximately 5.0 mm |
| Color of Secondary Branches | RHS 144A (Strong Yellow Green) with anthocyanin RHS 187B (Dark Red) at nodes |
| Life Cycle | Annual |
| Time to produce a rooted cutting: | About 4 weeks |
| Time to bloom from propagation: | 6 to 8 Weeks |
| Flowering requirements (season): | Will flower so long as temperature is above 5° C. |
| Resistance/susceptibility: | No particular resistance or susceptibility observed |
| Temperature tolerances: | Plants observed to continue flowering in a temperature range of 5° C. to 36° C. |
| Stems | |
| Stem Color: | RHS 144A (Strong Yellow Green) |
| Stem anthocyanin: | RHS 187B (Dark Red) at nodes |
| Stem pubescence: | Glabrous |
| Stem pubescence color: | None |
| Stem description: | Strong; circular cross—section, smooth and shiny |
| Stem Length: | Approximately 2.0 cm to 6.0 cm from branch to inflorescence |
| Stem Diameter: | Approximately 4.0 mm |
| Internode Length: | Approximately 1.5 cm to 3.5 cm |

TABLE 1-continued

VARIETY DESCRIPTION INFORMATION

| Characteristic | SAKIMP062 |
|---|---|
| Leaves | |
| Leaf Arrangement: | Whorled with up to 5 leaves per node, opposite if only two leaves at one node |
| Leaf Shape: | Lanceolate |
| Leaf Tip: | Acuminate |
| Leaf Base: | Shortly attenuate |
| Leaf margin: | Serrate |
| Leaf surface: | Smooth, waxy |
| Leaf Pubescence: | None observed |
| Leaf Length: | Up to approximately 10.0 cm for larger leaves |
| Leaf Width: | Up to approximately 5.0 cm for larger leaves |
| Leaf Color—Upper: | Closest to but darker than NN137A (Greyish Olive Green) |
| Leaf Color—Lower: | Closest to but lighter than 147B (Moderate Yellow Green) |
| Leaf Variegation: | None |
| Leaf Fragrance: | None |
| Petiole Length: | Up to approximately 1.5 cm |
| Petiole Diameter: | Up to approximately 3.0 mm |
| Petiole Color | Closest to but lighter than 145B (Light Yellow Green) |
| Petiole Texture: | Smooth; Glabrous |
| Petiole Pubescence: | None |
| Leaf Venation Color—Upper: | 145B (Light Yellow Green) |
| Leaf Venation Color—Lower: | Closest to 147C (Moderate Yellow Green) |
| Flower | |
| Number of Flowers per node: | 1 to 3 in bloom at one time; about 3 to 5 flower buds |
| Number of Flowers per plant: | Approximately 13 |
| Lastingness of Blooms: | About 14 days |
| Flower Inflorescence Type: | Single flower with spur |
| Flower Fragrance: | Absent |
| Corolla Shape: | Roughly circular with 5 radial petals |
| Corolla Diameter: | Approximately 5.0 cm |
| Corolla Depth: | Approximately 4.0 mm |
| Sepal Shape: | Lanceolate |
| Sepal Number: | 2 |
| Sepal Base: | Sub cordate |
| Sepal Apex: | Caudate |
| Sepal Margin: | Entire |
| Sepal Texture: | Glabrous |
| Sepal Color—Upper | Background of 155C (Greenish White) with 144B (Strong Yellow Green) and 144A (Strong Yellow Green) at the tip and spots of 60C (Strong Purplish Red) |
| Sepal Color—Lower | Background of 155C (Greenish White) with 144B (Strong Yellow Green) and 144A (Strong Yellow Green) at the tip |
| Sepal Length: | Approximately 13.0 mm |
| Sepal Width: | Approximately 6.0 mm |
| Bud | |
| Bud Surface | Smooth, glabrous |
| Bud Length | Approximately 16.0 mm |
| Bud Diameter | Approximately 12.0 mm |
| Bud Shape: | Deltoid longitudinal cross-section |
| Bud Color: | 72B (Strong Reddish Purple) with 144A Strong Yellow Green) at edge |
| Peduncle Length | Approximately 4.5 cm |
| Peduncle width | Approximately 2.0 mm |
| Peduncle Texture | Smooth, glabrous |
| Peduncle Color | 145C (Light Yellow Green) with spots of 60C (Strong Purplish Red) on some |
| Petal Pubescence | None |
| Petal Length | Upper: 2.4 cm<br>Lower: 2.9 cm<br>Lateral: 2.5 cm |
| Petal Width | Upper: 4.0 cm<br>Lower: 3.4 cm<br>Lateral: 2.8 cm |
| Petal Shape | Obcordate |
| Petal Apex | Emarginate (cleaved) |
| Petal margin | Entire |
| Petal Base | Attenuate |
| Petal Color - Upper: | Closest to N78A (Strong Reddish Purple) |
| Petal Color - Lower: | Closest to N78B (Strong Reddish Purple) |
| Petal Color - Eye Zone: | Closest to but slightly redder than 61A (Deep Purplish Red) |

TABLE 1-continued

VARIETY DESCRIPTION INFORMATION

| Characteristic | SAKIMP062 |
|---|---|
| Spur | |
| Spur Color: | N155A (Pinkish White) background color with 71B (Strong Purplish red) at base, Pale 60C (Strong Purplish Red) on tube, transitioning to N144C Strong Yellow Green) at tip. |
| Spur Shape: | Tubular, curved downward |
| Spur Length: | Approximately 7.8 cm |
| Spur Diameter: | Approximately 1.5 mm |
| Stamens | |
| Stamen Form: | Fused; split into 4 lobes |
| Stamen Number: | 1 |
| Anther Length: | 5.0 mm |
| Anther Color: | 71A (Deep Purplish Red) |
| Pistils | |
| Pistil Number: | 1 |
| Pistil Length | 4.5 mm |
| Stigma Color: | 154C (Brilliant Yellow Green) |
| Style Color: | 144C (Strong Yellow Green) |
| Ovary Arrangement: | Parietal |
| Ovary Surface Color: | 154D (Light Yellow Green) |
| Pollen & Seeds | |
| Pollen Amount: | Moderate at time of collection |
| Pollen Color | 155D (Yellowish White) |
| Pollen Description | Powdery |
| Seed Production: | None Observed |

SAKIMP062 is most similar to the commercial Impatiens variety 'SAKIMP051' (U.S. Pat. No. 10,687,491), however, there are differences as listed in the table below.

TABLE 2

COMPARISON OF SAKIMP062 WITH 'SAKIMP051'

| | SAKIMP062 | SAKIMP051 |
|---|---|---|
| Flower Color, Upper | Closest to N78A (Strong Reddish Purple) | Closest to but darker and brighter than RHS N74A (Vivid Reddish Purple) |
| Petal Eye Zone | Closest to but slightly redder than 61A (Deep Purplish Red) | Closest to but brighter than RHS 64A (Moderate Purplish Red) |

SAKIMP062 can be compared with its parental lines, as shown in Table 3:

TABLE 3

COMPARISON OF SAKIMP062 WITH PARENTAL LINES

| | SAKIMP062 | Female Parent 'NM-2124-7H' | Male Parent 'NN-1616wB' |
|---|---|---|---|
| Flower Color | Purple | Magenta | Rose |
| Plant Habit | Compact | More vigorous than SAKIMP062 | More vigorous than SAKIMP062 |
| Flower Size | Approximately 5.0 cm | Smaller than SAKIMP062 | Similar to SAKIMP062 |

Further Embodiments

Breeding with New Guinea Impatiens SAKIMP062

The goal of ornamental plant breeding is to develop new, unique and superior ornamental plants. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same genetic variety, having the same traits from the exact same parents.

Each year, the plant breeder selects the germplasm to advance to the next generation. This germplasm is grown under unique and different geographical climatic and soil conditions and further selections are then made during and at the end of the growing season. The varieties that are developed are unpredictable because the breeder's selection occurs in unique environments with no control at the DNA level, and with millions of different possible genetic combinations being generated. A breeder of ordinary skill in the art cannot predict the final resulting lines he develops, except possibly in a very gross and general fashion. The same breeder cannot produce the same variety twice by using the same original parents and the same selection techniques. This unpredictability results in the expenditure of large amounts of research monies to develop superior impatiens varieties.

Breeding programs combine desirable traits from two or more varieties or various broad-based sources into breeding pools from which varieties are developed by selfing and selection of desired phenotypes. Pedigree breeding is used commonly for the improvement of self-pollinating plants. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Using New Guinea Impatiens SAKIMP062 to Develop Other Plants

SAKIMP062 plants can also provide a source of breeding material that may be used to develop new impatiens plants and varieties. Plant breeding techniques known in the art and used in an impatiens plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, making double haploids, mutagenesis and transformation. Often combinations of these techniques are used. The development of impatiens varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

Any plants produced using the SAKIMP062 plants disclosed in the present application as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); and Vainstein, "Breeding for Ornamentals: Classical and Molecular Approaches," Kluwer Academic Publishers (2002); Callaway, "Breeding Ornamental Plants," Timber Press (2000).

Breeding steps that may be used in the New Guinea Impatiens SAKIMP062 plant breeding program can include for example, pedigree breeding, backcrossing, mutation breeding, and recurrent selection. In conjunction with these steps, techniques such as RFLP-enhanced selection, genetic marker enhanced selection (for example, SSR markers), Gene Editing and the making of double haploids may be utilized.

As used herein, the term "plant" includes plant cells, plant protoplasts, plant cell tissue cultures from which SAKIMP062 plants can be regenerated, plant calli, plant clumps, and plant cells that are intact in plants or parts of plants, such as pollen, ovules, embryos, protoplasts, meristematic cells, callus, leaves, anthers, cotyledons, hypocotyl, pistils, roots, root tips, seeds, flowers, petiole, shoot, or stems and the like.

Pedigree Breeding

Pedigree breeding starts with the crossing of two genotypes, such as New Guinea Impatiens SAKIMP062 and another different impatiens plant having one or more desirable characteristics that is lacking or which complements the New Guinea Impatiens SAKIMP062 phenotype. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent. This is also known as single gene conversion and/or backcross conversion.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a New Guinea Impatiens plant may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new New Guinea Impatiens varieties.

Therefore, another embodiment is a method of making a backcross conversion of New Guinea Impatiens SAKIMP062, comprising the steps of crossing New Guinea Impatiens SAKIMP062 with a donor plant comprising a desired trait, selecting an $F_1$ progeny plant comprising the desired trait, and backcrossing the selected $F_1$ progeny plant to New Guinea Impatiens SAKIMP062. This method may further comprise the step of obtaining a molecular marker profile of New Guinea Impatiens SAKIMP062 and using the molecular marker profile to select for a progeny plant with the desired trait and the molecular marker profile of New Guinea Impatiens SAKIMP062.

Recurrent Selection and Mass Selection

Recurrent selection is a method used in a plant breeding program to improve a population of plants. New Guinea Impatiens SAKIMP062 is suitable for use in a recurrent selection program. The method entails individual plants cross-pollinating with each other to form progeny. The progeny are grown and the superior progeny selected by any number of selection methods, which include individual plant, half-sib progeny, full-sib progeny, and selfed progeny. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Protoplast Fusion

Also known as somatic fusion, this process can be used with SAKIMP062 to create hybrids. The resulting hybrid plants have the chromosomes of each parent and thus the process is useful for incorporating new traits. The protoplast fusion technique is well known in the art; see for example Hamill J. D., Cocking E. C. (1988) Somatic Hybridization of Plants and its Use in Agriculture. In: Pais M. S. S., Mavituna F., Novais J. M. (eds) *Plant Cell Biotechnology*. NATO ASI Series (Series H: *Cell Biology*), vol 18.

Mutation Breeding

Mutation breeding is another method of introducing new traits into New Guinea Impatiens SAKIMP062. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methylnitrilsourea, or acridines; TILLING (targeting induced local lesions in genomes), where mutation is induced by chemical mutagens and mutagenesis is accompanies by the isolation of chromosomal DNA from every mutated plant line or seed and screening of the population of the seed or plants is performed at the DNA level using advanced molecular techniques. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002); Sikora, Per, et al., "Mutagenesis as a Tool in Plant Genetics, Functional Genomics, and Breeding" *International Journal of Plant Genomics*. 2011 (2011); 13 pages. In addition, mutations created in other New Guinea Impatiens plants may be used to produce a backcross conversion of New Guinea Impatiens that comprises such mutation.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s *in E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system. See for example, U.S. Application Publication No. WO2014068346 (György et al., Identification of a *Xanthomonas euvesicatoria* resistance gene from pepper (*Capsicum annuum*) and method for generating plants with resistance); Martinelli, F. et al., "Proposal of a Genome Editing System for Genetic Resistance to Tomato Spotted Wilt Virus" *American Journal of Applied Sciences* 2014; Noman, A. et al., "CRISPR-Cas9: Tool for Qualitative and Quantitative Plant Genome Editing" *Frontiers in Plant Science Vol.* 7 Nov. 2016; and "Exploiting the CRISPR/Cas9 System for Targeted Genome Mutagenesis in Petunia" *Science Reports* Volume 6: February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on New Guinea Impatiens SAKIMP062 to modify traits and resistances or tolerances to pests, herbicides, diseases, and viruses.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing using SAKIMP062.

The technique is well known in the art; see for example Malzahn, Aimee et al. "Plant genome editing with TALEN and CRISPR" *Cell & bioscience* vol. 7 21. 24 Apr. 2017.

Therefore, it is another embodiment to use the TALENs system on New Guinea Impatiens variety SAKIMP062 to modify traits and resistances or tolerances to pests, herbicides, and viruses.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51 (1): pp. 1-8 (2015); and Daboussi, Fayza, et al. "Engineering Meganuclease for Precise Plant Genome Modification" in Advances in New Technology for Targeted Modification of Plant Genomes. Springer Science+Business. pp 21-38 (2015).

Therefore, it is another embodiment to use engineered nucleases on New Guinea Impatiens variety SAKIMP062 to modify traits and resistances or tolerances to pests, herbicides, and viruses.

Additional Methods of Transformation

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject New Guinea Impatiens SAKIMP062 plants are intended to be within the scope of the embodiments of the application.

Single-Gene Conversions

When the term New Guinea Impatiens SAKIMP062 plant is used in the context of an embodiment of the present application, this also includes any single gene conversions of New Guinea Impatiens SAKIMP062. The term single gene converted plant as used herein refers to those impatiens plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental New Guinea Impatiens plant that contributes the gene for the desired characteristic is termed the nonrecurrent or donor parent. This terminology refers to the fact that the nonrecurrent parent is used one time in the backcross protocol and therefore does not recur. The parental New Guinea Impatiens plant to which the gene or genes from the nonrecurrent parent are transferred is known as the recurrent parent as it is used for several rounds in the backcrossing protocol (Poehlman & Sleper (1994). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a New Guinea Impatiens plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially important trait or traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety but that can be improved by backcrossing techniques. These traits are well-known in the art.

Introduction of a New Trait or Locus into New Guinea Impatiens SAKIMP062

New Guinea Impatiens SAKIMP062 represents a new base of genetics into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of New Guinea Impatiens SAKIMP062

A backcross conversion of New Guinea Impatiens SAKIMP062 occurs when DNA sequences are introduced through backcrossing (Allard, "Principles of Plant Breeding" (1999) with New Guinea Impatiens SAKIMP062 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, *Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. See, Allard, "Principles of Plant Breeding" (1999). Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into New Guinea Impatiens SAKIMP062 is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

In addition, the above process and other similar processes described herein may be used to produce first generation progeny impatiens seed by adding a step at the end of the process that comprises crossing New Guinea Impatiens SAKIMP062 with the introgressed trait or locus with a different plant and harvesting the resultant first generation progeny seed.

Molecular Techniques Using New Guinea
Impatiens SAKIMP062

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding With Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing New Guinea Impatiens SAKIMP062. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in *Brassica napus*" *Journal of Experimental Biology.* 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a New Guinea Impatiens plant for which New Guinea Impatiens SAKIMP062 is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see, Ferrie, Alison M. R., et al., "Review of Doubled Haploidy Methodologies in Ornamental Species" *Propagation of Ornamental Plants.* 11 (2): pp. 63-77 (2011).

Thus, an embodiment is a process for making a substantially homozygous New Guinea Impatiens SAKIMP062 progeny plant by producing or obtaining a seed from the cross of New Guinea Impatiens SAKIMP062 and another impatiens plant and applying double haploid methods to the $F_1$ seed or $F_1$ plant or to any successive filial generation.

In particular, a process of making seed retaining the molecular marker profile of New Guinea Impatiens SAKIMP062 is contemplated, such process comprising obtaining or producing $F_1$ seed for which New Guinea Impatiens SAKIMP062 is a parent, inducing doubled haploids to create progeny without the occurrence of meiotic segregation, obtaining the molecular marker profile of New Guinea Impatiens SAKIMP062, and selecting progeny that retain the molecular marker profile of New Guinea Impatiens SAKIMP062.

Expression Vectors for New Guinea Impatiens Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci.* USA, 84:131 (1987); DeBlock, et al., *EMBO J.,* 3:1681 (1984)).

Expression Vectors for New Guinea Impatiens Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.,* 20:49 (1992); Knox, C., et al., *Plant Mol. Biol.,* 9:3-17 (1987); Lerner, et al., *Plant Physiol.,* 91:124-129 (1989); Frontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.* 2:129 (1991); Kalderon, et al., *Cell,* 39:499-509 (1984); Steifel, et al., *Plant Cell,* 2:785-793 (1990).

Foreign Protein Genes: Transformation

Various promoters, targeting sequences, enhancing sequences, and other DNA sequences can be inserted into the genome for the purpose of altering the expression of genes Gene Silencing and Altering Gene Expression Many techniques for altering gene expression are well-known to one of skill in the art, including, but not limited to, knock-outs (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA*, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8 (12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); transposable elements (e.g. Dubin, M. J., et al., Transposons: a blessing curse, *Current opinion in plant biology*, Vol: 42, Page: 23-29, 2018 and Eric T. Johnson, Jesse B. Owens & Stefan Moisyadi (2016) Vast potential for using the piggyBac transposon to engineer transgenic plants at specific genomic locations, *Bioengineered*, 7:1, 3-6); and other methods or combinations of the above methods known to those of skill in the art.

Additional Transformation Embodiments

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular New Guinea Impatiens line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, commercially important genes can be expressed in transformed plants. More particularly, plants can be genetically engineered to express various phenotypes of commercial interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Many hundreds if not thousands of different genes are known and could potentially be introduced into a New Guinea Impatiens plant according to the invention. Non-limiting examples of particular genes and corresponding phenotypes one may choose to introduce into a New Guinea Impatiens plant include one or more genes for insect tolerance, such as a *Bacillus thuringiensis* (Bt.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of one or more embodiments.

Tissue Culture

Further reproduction of the variety can occur by tissue culture and regeneration. Tissue culture of various tissues of ornamental plants and New Guinea Impatiens SAKIMP062 and regeneration of plants therefrom is well-known and widely published. For example, reference may be had to do Valla Rego, Luciana et al., Crop Breeding and Applied Technology. 1 (3): 283-300 (2001); Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992). Thus, another embodiment is to provide cells which upon growth and differentiation produce New Guinea Impatiens plants having the physiological and morphological characteristics of New Guinea Impatiens SAKIMP062 described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, pollen, leaves, ovules, anthers, cotyledons, hypocotyl, pistils, roots, root tips, flowers, seeds, petiole, shoot, or stems, and the like. Means for preparing and maintaining plant tissue culture are well-known in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

DEPOSIT INFORMATION

A deposit of the Sakata Seed Corporation proprietary New Guinea Impatiens variety SAKIMP062 plant tissue disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Me. 04544. The date of deposit was Dec. 28, 2021. The NCMA No. is 202112022. The deposit of plant tissue was taken from the same deposit maintained by Sakata Seed Corporation since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

What is claimed is:

1. A plant of New Guinea Impatiens variety SAKIMP062, wherein a representative sample of plant tissue of SAKIMP062 was deposited under NCMA No. 202112022.

2. A plant, or a plant part thereof produced by growing the plant of claim 1, wherein the plant or plant part comprises at least one cell of New Guinea Impatiens variety SAKIMP062.

3. A New Guinea Impatiens plant, or part thereof, having all of the physiological and morphological characteristics of the New Guinea Impatiens plant of claim 1.

4. A tissue or cell culture of regenerable cells produced from the plant of claim 1.

5. The tissue or cell culture of claim 4, comprising tissues or cells from a plant part selected from the group consisting of leaves, pollen, embryos, cotyledons, hypocotyl, meristematic cells, roots, root tips, pistils, anthers, flowers, and stems.

6. A New Guinea Impatiens plant regenerated from the tissue or cell culture of claim 5, wherein said plant has all of the morphological and physiological characteristics of New Guinea Impatiens SAKIMP062.

7. A method of vegetatively propagating the plant of claim 1, comprising the steps of:
   collecting tissue or cells capable of being propagated from said plant;
   cultivating said tissue or cells to obtain proliferated shoots; and
   rooting said proliferated shoots to obtain rooted plantlets; or
   cultivating said tissue or cells to obtain proliferated shoots, or to obtain plantlets.

8. A New Guinea Impatiens plant produced by growing the plantlets or proliferated shoots of claim 7.

9. A method for producing an embryo or seed, wherein the method comprises crossing the plant of claim 1 with another plant and harvesting the resultant embryo or seed.

10. A method of determining the genotype of the New Guinea Impatiens plant of claim 1, wherein said method comprises obtaining a sample of nucleic acids from said plant and detecting in said nucleic acids a plurality of polymorphisms.

11. A method of producing a New Guinea Impatiens plant resistant to the group consisting of herbicides, insecticides, and disease, wherein the method comprises transforming the New Guinea Impatiens plant of claim 1 with a transgene, and wherein said transgene confers resistance to an herbicide, insecticide, or disease.

12. An herbicide, insecticide, or disease resistant plant produced by the method of claim 11.

13. A method for developing a New Guinea Impatiens plant in a plant breeding program, comprising applying plant breeding techniques comprising crossing, recurrent selection, mutation breeding, wherein said mutation breeding selects for a mutation that is spontaneously or naturally induced or artificially induced, backcrossing, pedigree breeding, marker enhanced selection, haploid/double haploid production, or transformation to a plant of New Guinea Impatiens variety SAKIMP062, wherein a representative sample of plant tissue of SAKIMP062 was deposited under NCMA No. 202112022, or its parts, wherein application of said techniques results in development of a New Guinea Impatiens plant.

14. A method of introducing a mutation into the genome of New Guinea Impatiens plant SAKIMP062, said method comprising mutagenesis of the plant, or plant part thereof, of claim 1, wherein said mutagenesis is selected from the group consisting of temperature, long-term seed storage, tissue culture conditions, ionizing radiation, chemical mutagens, or targeting induced local lesions in genomes, and wherein the resulting plant comprises at least one genome mutation.

15. A method of editing the genome of New Guinea Impatiens plant SAKIMP062, wherein a representative sample of plant tissue of SAKIMP062 was deposited under NCMA No. 202112022, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

16. A New Guinea Impatiens plant produced by the method of claim 15, wherein said plant is produced by editing the genome of said plant and otherwise contains all of the morphological and physiological characteristics of New Guinea Impatiens SAKIMP062.

17. A New Guinea Impatiens seed produced by growing the plant of claim 1.

18. A method of producing a New Guinea Impatiens plant, or part thereof, produced by growing the seed of claim 17.

19. A seed produced by the method of claim 9, wherein the female parent is SAKIMP062.

20. The method of claim 9, further comprising producing a plant, or a part thereof, from the resultant embryo or seed.

* * * * *